United States Patent [19]

Herrin

[11] 4,262,367
[45] Apr. 21, 1981

[54] SUN VISOR

[75] Inventor: Lenny Herrin, Elkins Park, Pa.

[73] Assignee: Regent Paper Box Co., Inc., Philadelphia, Pa.

[21] Appl. No.: 456

[22] Filed: Jan. 2, 1979

[51] Int. Cl.³ .................................................. A61F 9/04
[52] U.S. Cl. ........................................... 2/12; 40/586
[58] Field of Search ............... 2/12, 195, 200, 175, 2/192, 171, 174, 177; 264/22, 26; 40/586

[56] References Cited

U.S. PATENT DOCUMENTS

| 2,530,881 | 11/1950 | Houston | 2/12 |
| 3,470,639 | 10/1969 | Ihling | 40/586 |
| 4,064,206 | 12/1977 | Seufert | 264/22 X |
| 4,106,119 | 8/1978 | Taupin | 2/12 |

FOREIGN PATENT DOCUMENTS

| 1025669 | 1/1953 | France | 2/12 |
| 180805 | 11/1935 | Switzerland | 2/12 |
| 343079 | 2/1931 | United Kingdom | 2/12 |

*Primary Examiner*—Peter P. Nerbun
*Attorney, Agent, or Firm*—Howson and Howson

[57] ABSTRACT

A flexible visor portion is generally U-shaped with a curved inner periphery extending to leg portions. A string extends between the leg portions. At least two flanges are integral with the visor portion at the inner periphery thereof and are connected thereto by a hinge.

3 Claims, 4 Drawing Figures

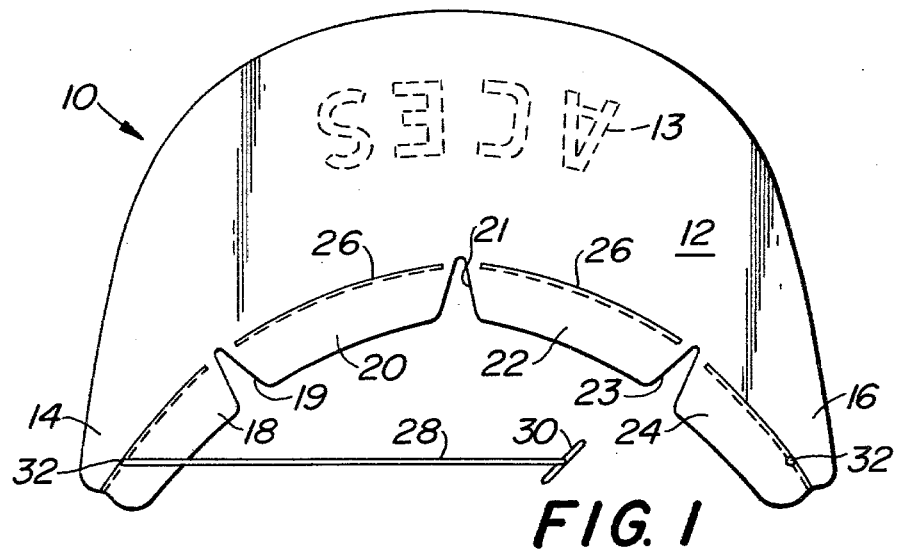
FIG. 1
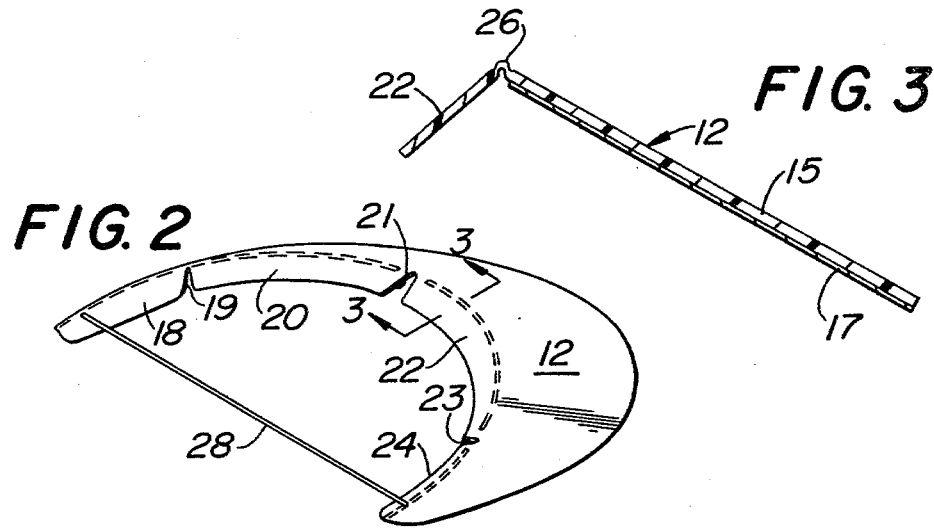
FIG. 3
FIG. 2
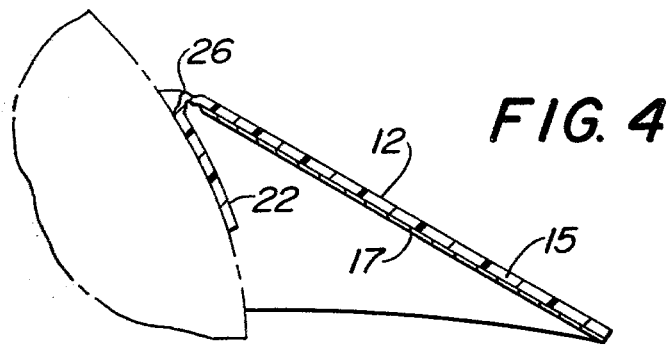
FIG. 4

4,262,367

SUN VISOR

BACKGROUND

Sun visors which have a generally U-shaped periphery and string means extending between the leg portions are old and well known. The inner periphery of such a sun visor made from a plastic material has a cutting effect which is more pronounced as compared with a similar visor made from paper. Sun visors made from paper are limited in that they cannot be used in inclement weather. A sun visor made from a plastic material is more desirable and practical but has not been used to any great extent heretofore due to the cutting effect of the inner periphery of the visor portion on the forehead of the wearer.

The present invention is directed to a sun visor which minimizes the cutting effect of the inner periphery of the visor portion on the forehead of the wearer.

SUMMARY OF THE INVENTION

The present invention is directed to a sun visor having a flexible visor portion which is generally U-shaped and having a curved inner periphery extending to leg portions. A string means extends between the leg portions and is adapted to extend around the rear portion of a wearer's head. At least two flanges are integral in one piece with the visor portion at the inner periphery of the visor portion. The flanges are connected to the visor portion by a hinge. The flanges are spaced from one another at a gap adjacent the bight portion of the inner periphery of the visor portion.

It is an object of the present invention to provide a novel sun visor which minimizes the cutting effect at the inner periphery of the sun visor on the forehead of the wearer.

Other objects will appear hereinafter.

For the purpose of illustrating the invention, there is shown in the drawings a form which is presently preferred; it being understood, however, that this invention is not limited to the precise arrangements and instrumentalities shown.

FIG. 1 is a top plan view of a sun visor in accordance with the present invention.

FIG. 2 is a perspective view of a sun visor in accordance with the present invention.

FIG. 3 is a sectional view taken along the line 3—3 in FIG. 2 but on an enlarged scale.

FIG. 4 is a sectional view similar to FIG. 3 but illustrating the components in the position which they assume while the sun visor is worn by a person.

Referring to the drawings in detail, wherein like numerals indicate like elements, there is shown in FIG. 1 a sun visor in accordance with the present invention designated generally as 10. The sun visor 10 includes a visor portion 12 having a curved inner periphery extending to leg portions 14 and 16.

The visor portion may be made from any one of a wide variety of polymeric thermoplastic materials such as polyvinylchloride, polyethylene, etc. The visor portion 12 is preferably made wherein layer 15 is a layer of transparent thermoplastic material such as plasticizer free, hard PVC having high impact resistance and a K-value of 60. Layer 15 preferably has a thickness of about 0.010 to 0.015 inches.

The material of layer 15 is preferably chosen so that it may have indicia applied thereto by printing, hot stamping, silk screening, or the like. Referring to FIGS. 1 and 3, indicia 13 and an opaque background 17 are applied to the layer 15. Indicia 13 may be a name, a trademark, a cartoon character, or a combination thereof. When layer 15 is transparent, indicia 13 and background 17 are visible through layer 15.

At least two flanges are integral in one piece with the visor portion 12 and connected thereto by a living hinge. Referring to FIGS. 1 and 2, flanges 20 and 22 are integral in one piece with the layer 15 of the visor portion 12 and connected thereto by a discrete living hinge 26. The arcuate inner periphery of each flange and each hinge are curved parallel lines. While the hinges 26 are preferably discrete, one continuous hinge could be used. The flanges 20 and 22 are spaced from one another at the bight portion of the curved inner periphery of the visor portion 12 by the notch or gap 21 which projects past the hinges 26.

The flanges 20 and 22 need not extend to the ends of the curved inner periphery of the visor portion 12. If flanges are desired along the entire inner periphery, a flange 18 may be provided and spaced from flange 20 by the gap 19 and flange 24 may be provided. Flange 24 is spaced from the flange 22 by the gap 23.

Each hinge 26 is preferably of the type known in the art as a living hinge since its point of flexure is thinner than the material of the components joined thereby. Hinge 26 is preferably of the type shown in FIG. 4 of U.S. Pat. No. 4,064,206.

As shown in FIG. 1, when the sun visor 10 is manufactured, the flanges and the visor portion 12 are planar. When the sun visor 10 is worn, as shown in FIG. 4, the included angle between flange 22 and the visor portion 12 is about 30° to 60°. After being worn, the flanges assume the position shown in FIGS. 2 and 3. In order that the sun visor 10 may be retained on the forehead of a wearer, the leg portions 14 and 16 are interconnected by a string 28. String 28 is preferably an elastomeric string having retainers 30 on each end. Retainers 30 on each end are readily insertable through the holes 32 at the hinges. The retainers 30 are conventional and have been used heretofore in connection with face masks or the like.

Due to the provision of the flanges 20, 22 and the hinge 26, there is no sharp edge on the inner periphery of the sun visor 10 which cuts into the forehead of the wearer. Hence, the sun visor 10 of the present invention is more comfortable. Since the sun visor 10 is made from a polymeric thermoplastic, it may be worn during inclement weather without being damaged and can be made at low cost and at high production speeds with minimal labor. Since indicia 13 is on the inner or bottom surface of layer 15, it is less likely to be scratched or marred.

The present invention may be embodied in other specific forms without departing from the spirit or essential attributes thereof and, accordingly, reference should be made to the appended claims, rather than to the foregoing specification, as indicating the scope of the invention.

I claim:

1. A sun visor comprising a plastic visor portion which is generally U-shaped and having a curved inner periphery extending to leg portions, elastomeric string means extending between said leg portions, and string means being adapted to extend around the rear portion of a wearer's head, an even number of discrete flanges at the inner periphery of the visor portion, a discrete hinge for each flange, the ends of adjacent hinges being spaced from one another, each hinge being a discrete living hinge, each flange being spaced from an adjacent flange by a gap, one of said gaps being adjacent the center of the bight portion of the inner periphery of said visor portion, said gaps being V-shaped with curved apexes and extending between the ends of two adjacent hinges, each gap being deeper than the width of said flanges so that said gaps extend beyond the ends of adjacent hinges and into the visor portion, said visor portion having indicia on a surface thereof, and each hinge being integral on one piece with said visor portion and one of said flanges.

2. A sun visor in accordance with claim 1 wherein the inner peripheries of said visor portion and said flanges are curved substantially parallel lines.

3. A sun visor in accordance with claim 1 wherein the visor portion surface containing said indicia is a bottom surface thereof, said visor portion being made from a transparent or translucent polymeric thermoplastic material, said indicia being visible while observing the upper surface of said visor portion, and an opaque background applied to the bottom surface of said visor portion, the color of the background being different from the color of the indicia.

* * * * *